US012599548B2

(12) United States Patent
Hakozaki et al.

(10) Patent No.: US 12,599,548 B2
(45) **Date of Patent: *Apr. 14, 2026**

(54) METHOD OF TREATING OXIDATIVE STRESS IN SKIN AND COMPOSITIONS THEREFOR

(71) Applicant: The Procter & Gamble Company, Cincinnati, OH (US)

(72) Inventors: Tomohiro Hakozaki, Cincinnati, OH (US); Leo Timothy Laughlin, II, Mason, OH (US); Matthew Clair Ehrman, Singapore (SG); XiPing Ng, Singapore (SG)

(73) Assignee: The Procter & Gamble Company, Ciincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/732,895

(22) Filed: Jun. 4, 2024

(65) Prior Publication Data

US 2024/0315946 A1 Sep. 26, 2024

Related U.S. Application Data

(63) Continuation of application No. 17/549,980, filed on Dec. 14, 2021, now Pat. No. 12,036,302.

(60) Provisional application No. 63/125,011, filed on Dec. 14, 2020.

(51) Int. Cl.

| | |
|---|---|
| ***A61K 8/60*** | (2006.01) |
| ***A61K 8/34*** | (2006.01) |
| ***A61K 8/365*** | (2006.01) |
| ***A61K 8/67*** | (2006.01) |
| ***A61Q 19/08*** | (2006.01) |

(52) U.S. Cl.
CPC .............. *A61K 8/604* (2013.01); *A61K 8/342* (2013.01); *A61K 8/365* (2013.01); *A61K 8/675* (2013.01); *A61Q 19/08* (2013.01)

(58) Field of Classification Search
CPC ................................ A61K 8/604; A61Q 19/08
See application file for complete search history.

(56) References Cited

U.S. PATENT DOCUMENTS

| | | | |
|---|---|---|---|
| 3,755,560 | A | 8/1973 | Dickert et al. |
| 4,421,769 | A | 12/1983 | Dixon et al. |
| 5,011,681 | A | 4/1991 | Ciotti et al. |
| 5,766,575 | A | 6/1998 | Crotty et al. |
| 5,830,499 | A | 11/1998 | Bouwstra |
| 5,872,112 | A | 2/1999 | Blank |
| 5,939,082 | A | 8/1999 | Oblong et al. |
| 5,972,359 | A | 10/1999 | Sine et al. |
| 6,013,270 | A | 1/2000 | Hargraves |
| 6,174,533 | B1 | 1/2001 | Sanogueira, Jr. et al. |
| 6,238,678 | B1 | 5/2001 | Oblong et al. |
| H2013 | H | 2/2002 | Boyd et al. |
| 6,492,326 | B1 | 12/2002 | Robinson |
| 6,524,598 | B2 | 2/2003 | Sunkel et al. |
| 6,696,049 | B2 | 2/2004 | Vatter |
| 7,737,103 | B2 | 6/2010 | Hloucha |
| 7,754,775 | B2 | 7/2010 | Mercier et al. |
| 9,221,986 | B2 * | 12/2015 | Sujeeth ............... C09B 67/0086 |
| 9,446,265 | B2 | 9/2016 | Jansen et al. |
| 9,498,420 | B2 | 11/2016 | Laughlin, II |
| 9,757,317 | B2 | 9/2017 | Laughlin, II et al. |
| 9,795,552 | B2 | 10/2017 | Tanner et al. |
| 9,833,398 | B2 | 12/2017 | Hakozaki et al. |
| 9,949,917 | B2 | 4/2018 | Moussou et al. |
| 10,512,603 | B2 | 12/2019 | Almiñana Domènech et al. |
| 10,660,838 | B2 | 5/2020 | Hakozaki et al. |
| 10,874,600 | B2 | 12/2020 | Hakozaki et al. |
| 11,571,379 | B2 | 2/2023 | Hakozaki et al. |
| 11,968,993 | B2 | 4/2024 | Schoeppe |
| 2002/0022040 | A1 | 2/2002 | Robinson et al. |
| 2003/0049212 | A1 | 3/2003 | Robinson et al. |
| 2004/0175347 | A1 | 9/2004 | Bissett |
| 2004/0265258 | A1 | 12/2004 | Robinson et al. |
| 2005/0220726 | A1 | 10/2005 | Pauly et al. |
| 2005/0238677 | A1 | 10/2005 | Mercier |
| 2006/0165735 | A1 | 7/2006 | Abril et al. |
| 2006/0275237 | A1 | 12/2006 | Bissett |
| 2007/0196344 | A1 | 8/2007 | Osborne et al. |
| 2008/0181956 | A1 | 7/2008 | Ha et al. |
| 2008/0206373 | A1 | 8/2008 | Millikin et al. |

(Continued)

FOREIGN PATENT DOCUMENTS

| | | |
|---|---|---|
| CN | 103655313 A | 3/2014 |
| CN | 104027265 A | 9/2014 |

(Continued)

OTHER PUBLICATIONS

Boulier, V. et al. "New formulations containing a blend of sucrose laurates", Research Disclosure database No. 535032, Nov. 20008.*
"Sensitive Multi-Benefit Integral Care for Sensitive Skin", Mintel, Retrieved from URL Link: Http://www.gndp.com, Published on Feb. 2016, 7 pgs.
15943M PCT Search Report and Written Opinion for PCT/US2021/063194 dated Apr. 8, 2022, 20 pages.
All Office Actions; U.S. Appl. No. 17/549,980, filed Dec. 14, 2021.
All Office Actions; U.S. Appl. No. 17/155,151, filed Jan. 22, 2021.

(Continued)

*Primary Examiner* — Gina C Justice
(74) *Attorney, Agent, or Firm* — Alexandra S. Anoff; John G. Powell

(57) ABSTRACT

Cellular energy levels in skin cells affected by oxidative stress can be improved through the use of a skin care composition that includes a sucrose ester and a fatty alcohol present at a specific ratio. The fatty alcohol and sucrose ester, when incorporated into a skin care composition at a specific ratio, can provide a synergistic improvement in cellular ATP level for skin cells suffering from the effects of oxidative stress.

12 Claims, No Drawings

(56) References Cited

U.S. PATENT DOCUMENTS

| | | | |
|---|---|---|---|
| 2010/0004729 | A1 | 1/2010 | Chew et al. |
| 2010/0047296 | A1 | 2/2010 | Banowski et al. |
| 2010/0092408 | A1 | 4/2010 | Breyfogle et al. |
| 2010/0189669 | A1 | 7/2010 | Hakozaki |
| 2010/0239510 | A1 | 9/2010 | Ha et al. |
| 2010/0272667 | A1 | 10/2010 | Kyte, III et al. |
| 2011/0097286 | A1 | 4/2011 | Swanson |
| 2011/0262025 | A1 | 10/2011 | Jarrold et al. |
| 2012/0128603 | A1 | 5/2012 | Tanaka |
| 2012/0128683 | A1 | 5/2012 | Shantha |
| 2012/0148510 | A1 | 6/2012 | Hakozaki et al. |
| 2012/0148515 | A1 | 6/2012 | Hakozaki et al. |
| 2012/0156146 | A1 | 6/2012 | Hakozaki et al. |
| 2012/0197016 | A1 | 8/2012 | Laughlin, II et al. |
| 2013/0022557 | A1 | 1/2013 | Swanson et al. |
| 2014/0271506 | A1 | 9/2014 | Laughlin, II et al. |
| 2014/0328775 | A1 | 11/2014 | Laughlin, II et al. |
| 2015/0196464 | A1 | 7/2015 | Jansen et al. |
| 2016/0128924 | A1 | 5/2016 | Lee et al. |
| 2017/0348221 | A1 | 12/2017 | Maruyama |
| 2017/0348551 | A1 | 12/2017 | Doering et al. |
| 2018/0221256 | A1 | 8/2018 | Sunkel |
| 2018/0280282 | A1 | 10/2018 | Mcconaughy et al. |
| 2019/0380945 | A1 | 12/2019 | Hakozaki et al. |
| 2020/0009123 | A1 | 1/2020 | Hakozaki et al. |
| 2020/0178881 | A1 | 6/2020 | Purwar et al. |
| 2020/0253851 | A1 | 8/2020 | Hakozaki et al. |
| 2020/0405614 | A1 | 12/2020 | Hakozaki |
| 2020/0405621 | A1 | 12/2020 | Hakozaki |
| 2020/0405622 | A1 | 12/2020 | Paufique |
| 2021/0228469 | A1 | 7/2021 | Hakozaki et al. |
| 2022/0062155 | A1 | 3/2022 | Billinger |
| 2022/0183936 | A1 | 6/2022 | Ehrman et al. |
| 2022/0183948 | A1 | 6/2022 | Hakozaki et al. |

FOREIGN PATENT DOCUMENTS

| | | | |
|---|---|---|---|
| CN | 105456176 | A | 4/2016 |
| CN | 105560158 | A | 5/2016 |
| CN | 105662908 | A | 6/2016 |
| CN | 107308018 | A | 11/2017 |
| CN | 107595756 | A | 1/2018 |
| CN | 108379165 | A | 8/2018 |
| CN | 109620770 | A | 4/2019 |
| CN | 110101649 | A | 8/2019 |
| CN | 110314109 | A | 10/2019 |
| CN | 110547985 | A | 12/2019 |
| EP | 1216625 | A1 | 6/2002 |
| EP | 1842530 | A1 | 10/2007 |
| JP | 2000061289 | A | 2/2000 |
| JP | 2001031993 | A | 2/2001 |
| JP | 2002080370 | A | 3/2002 |
| JP | 2004154060 | A | 6/2004 |
| JP | 2005179237 | A | 7/2005 |
| JP | 2009209146 | A | 9/2009 |
| JP | 2014101378 | A | 6/2014 |
| JP | 2016030728 | A | 3/2016 |
| JP | 2017014135 | A | 1/2017 |
| JP | 2017061433 | A | 3/2017 |
| JP | 2017081848 | A | 5/2017 |
| JP | 2018039770 | A | 3/2018 |
| JP | 2018118931 | A | 8/2018 |
| JP | 2019014709 | A | 1/2019 |
| JP | 2019019077 | A | 2/2019 |
| JP | 2019085365 | A | 6/2019 |
| JP | 2020097549 | A | 6/2020 |
| WO | 9947141 | A1 | 9/1999 |
| WO | 2006040048 | A1 | 4/2006 |
| WO | 2007105706 | A1 | 9/2007 |
| WO | 2011074143 | A1 | 6/2011 |
| WO | 2012068357 | A2 | 5/2012 |
| WO | 2013049580 | A2 | 4/2013 |
| WO | 2018114742 | A1 | 6/2018 |
| WO | 2022132689 | A1 | 6/2022 |

OTHER PUBLICATIONS

All Office Actions; U.S. Appl. No. 17/549,989, filed Dec. 14, 2021.

All Office Actions; U.S. Appl. No. 18/074,577, filed Dec. 5, 2022.

Boulier et al., "New Formulations containing a blend of Sucrose Laurates", Sensient Cosmetic Technology, vol. 535, Nov. 1, 2008, 4 pages.

CHIfiger anti aging moisturizing and beauty, URL Link—http;//www.cosdna.com/chs/, dated Oct. 24, 2019, pp. 1-10.

Clear Lotion, ID 7622851, Mintel GNPD[online], May 2020, URL Link-, https://www.portal.mintel.com, dated Jul. 20, 2023, 5 pgs.

Cruces et al. "Improved Synthesis of Sucrose Fatty Acid Monoesters JAOCS", vol. 78, No. 5(2001) pp. 541-546. (Year: 2001).

Ice Eye Gel, ID 6159177, Mintel GNPD[online],Dec. 2018, URL, https://www.portal.mintel.com, Dated Jul. 20, 2023, 4 pgs.

Ixing, Revitalizing Skin Firming and Refining Emulsion, Liquid SPF 15, URL Linkhttp://www.cosdna.com/chs/, dated—Oct. 26, 2018, pp. 1-10.

Mitsubishi-Kagaku Foods Corporation; Anonymous: Ryoto Sugar Ester (Food Grade), Internet Citation, XP002557521, Retrieved from the internet: URL: http://web.archive.org/web20080524191629/http://www.mfc.co.jp/english/seihin.htm; retrieved on Nov. 26, 2009; pp. 01.

Miyamoto et al. Skin Res Technology , "Development of a Digital Imaging System for Objective Measurement of Hyperpigmented Spots on the Face;" Skin Res Technology 2002; 8:227-35.

Niacinamide—Mechanisms of Action and Its Topical Use in Dermatology, Skin Pharmacol Physiol 2014, Jun. 27, 2014, pp. 311-315.

The use of gene arrays and corresponding connectivity mapping (cMap) to identify novel anti-ageing ingredients, International Journal of Cosmetic Science (2015), vol. 37 issue S1, p. 9-14.

Unpublished U.S. Appl. No. 17/549,989, filed Dec. 14, 2021, to Matthew Clair Ehrman et al.

Unpublished U.S. Appl. No. 18/074,577, filed Dec. 5, 2022 to Tomohiro NMN Hakozaki et al.

Vermeire et al., "Sucrose Laurate Gels as a Percutaneous Delivery System for Oestradiol in Rabbits", Journal Of Pharmacy and Pharmacology, vol. 48, 1996, pp. 463-467.

"Lubrizol" Retrieved from https://www.lubrizol.com/-/media/Lubrizol/Personal-Care/Documents/Technical-Papers-and-Posters/MakeltSimple_Poster_DEC2012.pdf, Dec. 2012, 1 page.

"Stearyl Alcohol", Retrieved from https://pubchem.ncbi.nlm.nih.gov/compound/Stearyl-Alcohol, Aug. 10, 2020, 1 page.

* cited by examiner

METHOD OF TREATING OXIDATIVE STRESS IN SKIN AND COMPOSITIONS THEREFOR

FIELD

The present disclosure is directed generally to improving cellular energy levels in skin cells subjected to oxidative stress. More specifically, the present disclosure is directed to a combination of a sucrose ester and a fatty alcohol that synergistically improves cellular energy levels in skin cells subjected to oxidative stress.

BACKGROUND

A fundamental basis for life is the need and ability for cells to generate energy. In humans, food is taken in and ultimately converted into chemical compounds such as adenosine triphosphate ("ATP") for use by the cells of the body to perform the biological processes that sustain life. The metabolic pathways of the cells that convert the useful components of food (e.g., carbohydrates, fats and proteins) into usable energy are complex and may be affected by a variety of factors in ways that have not been completely elucidated. Mammalian skin cells are no exception. Skin cells are known to include a variety of different kinds of cells that functions together in a dynamic, complex relationship to maintain the health of the skin. For example, keratinocytes proliferate and differentiate to provide continuous skin turnover, melanocytes provide melanin synthesis for skin pigmentation, and fibroblasts synthesize the extracellular matrix to provide skin with thickness and elasticity. This, in order to maintain healthy skin, it is important for skin cells to produce energy as efficiently as possible and functional at an optimal level.

It is now known that a variety of environmental stressors can impact cellular bioenergetics and reduce the energy level of a skin cell, which may physically manifest as visible signs of aging (e.g., fine lines, wrinkles, uneven skin tone, hyperpigmented spots). One theory for why oxidative stress reduces cellular energy levels is that exposure to reactive oxygen species ("ROS") causes damage to cellular structures and organelles such as the mitochondria. ROS are highly reactive molecules that contain oxygen (e.g., oxygen ions and peroxides). In some instances, ROS are formed within cells as a natural byproduct of normal metabolism and play a role in cell signaling and homeostasis. However, when a cell is exposed to a stressor such as heat or UV radiation, ROS levels can increase dramatically, even to the point where the cell's antioxidant defense system is overwhelmed. When this happens, cell damage may occur.

Environmental stressors such as ultraviolet radiation ("UV") and pollutants (e.g., cigarette smoke, car exhaust, ozone) can lead to heightened levels of ROS production. As cellular damage caused by ROS accumulates over time, it results in oxidative stress at the cellular level that ultimately may lead to tissue damage and/or organ dysfunction. This damage typically manifests as noticeable changes in the skin's structure and morphology (e.g., "photodamage") and reduced ATP production. Thus, there is a continuing need for skin care actives that inhibit, prevent and/or reverse the reduction in cellular ATP production caused by oxidative stress.

SUMMARY

Provided herein are compositions and methods of improving cellular energy levels in skin cells affected by oxidative stress. The methods comprise identifying a target portion of skin where treatment is desired; and applying a skin care composition that includes a sucrose ester and a fatty alcohol, wherein a weight ratio of the fatty alcohol to the sucrose ester in the skin care composition is 1:4 to 40:1 and the combination of sucrose ester and fatty alcohol demonstrates a synergistic improvement in cellular adenosine triphosphate (ATP) levels according to the Oxidative Stress Test.

DETAILED DESCRIPTION

The undesirable effects of oxidative stress on skin function and appearance are known, and there are numerous skin care compositions marketed to treat the visible signs of skin aging. It has now been surprisingly discovered that combining a sucrose ester and a fatty alcohol at a specific ratio can provide a synergistic improvement in the ATP level of cells subjected to oxidative stress.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all ingredient percentages are based on the weight of the cosmetic composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive and combinable to form narrower ranges not explicitly disclosed. For example, delineated upper and lower range limits are interchangeable to create further ranges.

The compositions of the present invention can comprise, consist essentially of, or consist of, the essential components as well as optional ingredients described herein. As used herein, "consisting essentially of" means that the composition or component may only include additional ingredients that do not materially alter the basic and novel characteristics of the claimed composition or method. As used in the description and the appended claims, the singular forms "a", "an", and "the" are intended to include the plural forms as well, unless the context clearly indicates otherwise.

Definitions

"About" modifies a particular value by referring to a range equal to plus or minus twenty percent (+/−20%) or less (e.g., less than 15%, 10%, or even less than 5%) of the stated value.

"Agent" refers to a material, as well any component thereof, intended to provide a particular benefit or function. For example, an emollient agent is a material intended to provide an emolliency benefit to skin (e.g., a fatty alcohol), and a thickening agent is a material generally intended to increase the viscosity of a composition.

"Apply" or "application", as used in reference to a composition, means to apply or spread the compositions herein onto a bodily surface such as skin or hair.

"Cosmetic composition" means a composition that contains a cosmetic agent and is intended for non-therapeutic (i.e., non-medical) use. Examples of cosmetic compositions include color cosmetics (e.g., foundations, lipsticks, concealers, and mascaras), skin care compositions (e.g., moisturizers and sunscreens), personal care compositions (e.g., rinse-off and leave on body washes and soaps), hair care compositions (e.g., shampoos and conditioners).

"Derivative," herein, means amide, ether, ester, amino, carboxyl, acetyl, and/or alcohol derivatives of a given compound.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. In a specific example, an effective amount of sucrose ester and fatty alcohol is an amount sufficient to increase cellular ATP levels that have been reduced as a result of oxidative stress.

"Skin care" means regulating and/or improving a skin condition (e.g., skin health, appearance, or texture/feel). Some nonlimiting examples of improving a skin condition include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, barrier function, and/or cell metabolism).

"Skin care composition" means a composition that includes a skin care active and regulates and/or improves a skin condition.

"Synergy," and variations thereof, means that the effect provided by a combination of two or more materials (e.g., a sucrose ester and a fatty alcohol) is more than the additive effect expected for these materials. For example, synergy is demonstrated when a combination of a sucrose ester and a fatty alcohol increase cellular ATP levels by more than their calculated additive effect.

"Treatment period," as used herein, means the length of time and/or frequency that a material or composition is applied to a target skin surface.

Composition

The cosmetic compositions herein are intended for topical application to human skin and contain a synergistic combination of a sucrose ester and a fatty alcohol disposed in a dermatologically acceptable carrier. The combination of sucrose ester and fatty alcohol is sufficient to synergistically improve cellular ATP levels reduced as a result of oxidative stress. When used over the course of a treatment period (e.g., 2, 4 or 8 weeks), the synergistic combination of sucrose ester and fatty alcohol may improve the appearance of visible signs of skin aging. In some instances, the sucrose ester and fatty alcohol are present at a weight ratio of fatty alcohol to sucrose ester of 1:4 to 40:1 (e.g., 1:3, 1:2, 1:1, 2:1, 3:1, 4:1, 5:1, 10:1, 15:1, 20:1, 25:1, or even 30:1). The compositions herein may optionally include one or more additional skin actives or other ingredients of the type commonly included in topical skin care compositions.

The skin care compositions herein can be made using conventional methods of combining skin care composition ingredients. However, in some instances, it may be difficult to solubilize the sucrose ester in the composition using conventional methods. In these instances, it may be desirable to solubilize the sucrose ester in a glycol premix, which is then added to the composition. An example of this process is described in co-pending U.S. Provisional Ser. No. 63/124,870 filed on Dec. 14, 2020 by Tanaka, et al., and titled "Method of Manufacturing Cosmetic Compositions Comprising Sucrose Esters and Solvents."

The skin care compositions herein may be cosmetic compositions, pharmaceutical compositions, or cosmeceutical compositions, and may be provided in various product forms, including, but not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. In some instances, the composition form may follow from the particular dermatologically acceptable carrier chosen. For example, the composition (and carrier) may be provided in the form of an emulsion (e.g., water-in-oil, oil-in-water, or water-in-oil-in water) or an aqueous dispersion.

While it may be desirable to provide a skin care composition as an oil-in-water emulsion, the combination of sucrose ester and fatty alcohol may cause stability problems (phase separation, syneresis, etc.). Surprisingly, it has now been found that by selecting a particular type of thickener and emulsifier, the emulsion stability problems can be overcome. Some non-limiting examples of suitable thickeners and emulsifiers are described in more detail below. Other examples of stable emulsions containing sucrose esters are disclosed in co-pending U.S. Provisional Ser. No. 63/125,021, filed on Dec. 14, 2020 by Ehrman, et al., and titled "Stable Skin Care Emulsion and Methods of Using the Same."

Sucrose Ester

The compositions herein include an effective amount of an ester of sucrose and a fatty acid, wherein the fatty acid is selected from those with 12 to 24 carbon atoms (e.g., 12 to 22 carbon atoms or even 12 to about 18 carbon atoms). Particularly suitable fatty acids are selected from those with saturated alkyl groups. In some instances, the sucrose ester is selected from the group consisting of sucrose laurate, sucrose dilaurate, sucrose trilaurate, derivatives of these, and combinations thereof. As used herein, "sucrose laurate" means a compound having the formula $C_{24}H_{44}O_{12}$ and CAS

#25339-99-5; "sucrose dilaurate" means a compound having the formula $C_{36}H_{66}O_{13}$ and CAS #25915-57-5; and "sucrose trilaurate" means a compound having the formula $C_{48}H_{88}O_{14}$ and CAS #94031-23-9. The sucrose ester may be present at 0.0001% to 15% (e.g., 0.0002% to 10%, 0.001% to 15%, 0.025% to 10%, 0.05% to 7%, 0.05% to 5%, or even 0.1% to 3%) by weight of the composition.

In some instances, the sucrose ester may be a blend of two or more sucrose esters, wherein the two or more sucrose esters are present at a ratio of any one sucrose ester to another of 1:10 to 1:1 (e.g., 1:7, 1:5, 1:3, or 1:2). In some instances, the sucrose ester may be a blend of sucrose laurate and sucrose dilaurate, wherein sucrose laurate is present at 50% to 80%, by weight of the sucrose ester, and the sucrose dilaurate is present at 20% to 45%, by weight of the sucrose ester. Alternatively, the sucrose ester may be a blend of sucrose laurate, sucrose dilaurate and sucrose trilaurate, wherein sucrose dilaurate is present at 35% or more, by weight of the sucrose ester. A particularly suitable example of a sucrose ester for use herein is BC10034 from BASF, which is a blend of sucrose laurate and sucrose dilaurate. The BC10034 sucrose ester material can have a ratio of sucrose laurate to sucrose dilaurate ranging from 3:1 to 3:2.

Fatty Alcohol

The compositions herein include a fatty alcohol. Fatty alcohols refer to high-molecular-weight, straight-chain primary alcohols that have the general structure:

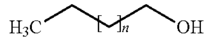

where n=8 to 32.

Fatty alcohols may be natural or synthetic, saturated or unsaturated, branched or straight-chain. Some nonlimiting examples of fatty alcohols commonly used in skin care compositions include caprylic, capryl, lauryl, myristyl, cetyl, stearyl, and behenyl alcohols. The fatty alcohols herein may be referred to generically by the number of carbon atoms in the molecule. For example, a "C12 alcohol" refers to an alcohol that has 12 carbon atoms in its chain (i.e., dodecanol). Some non-limiting examples of fatty alcohols that may be suitable for use herein are ricinoleates and 12-hydroxystearate. A particularly suitable fatty alcohol for use herein is hexyldecanol (CAS No. 2425-77-6), which has the structure:

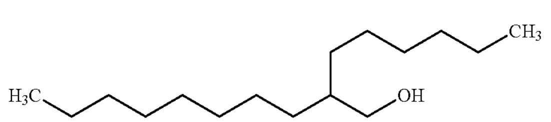 [SMILES: CCCCCCCCC(CO)CCCCCC]

The fatty alcohol may be included in the compositions herein at 0.0001% to 15% (e.g., 0.0002% to 10%, 0.001% to 15%, 0.025% to 10%, 0.05% to 7%, 0.05% to 5%, or even 0.1% to 3%) by weight of the composition.

Dermatologically Acceptable Carrier

The compositions disclosed herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion. The emulsion may have a continuous aqueous phase (e.g., an oil-in-water or water-in-oil-in-water emulsion) or a continuous oil phase (e.g., water-in-oil or oil-in-water-in-oil emulsion). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol (s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable, hydrophilic diluents. As used herein, "diluent" includes materials in which the sucrose ester can be dispersed, dissolved, or otherwise incorporated. Hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 425 to 2025 g/mole), glycerol, butylene glycol. 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Other Optional Ingredients

Compositions suitable for use in the method herein may include one or more optional ingredients known for use in topical skin care compositions, provided that the optional components do not unacceptably alter the desired benefits of the composition. In particular, the additional ingredients should not undesirably affect the ability of the sucrose ester fatty alcohol to synergistically increase cellular ATP levels reduced as a result of oxidative stress. In some instances, it may be desirable to select skin care actives that function via different biological pathways so that the actives do not interfere with one another. When the composition is in the form of an emulsion, the additional ingredients should not introduce instability into the emulsion (e.g., syneresis). For example, it may be desirable to select optional ingredients that do not form complexes with other ingredients in the composition, especially pH sensitive ingredients like vitamin B3 compounds, salicylates and peptides.

The additional ingredients should be suitable for use in contact with human skin tissue without undue toxicity, incompatibility, instability, allergic response, and the like. The optional components, when present, may be included at an amount of about 0.001% to 50% (e.g., 0.01% to 40%, 0.1% to 30%, 0.5% to 20%, or 1% to 10%), by weight of the composition. Some nonlimiting examples of additional ingredients include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunscreen agents, sunless tanning agents, lubricants, anti-acne agents, anti-cellulite agents, chelating agents, anti-wrinkle actives, anti-atrophy actives, phytosterols and/or plant hormones, N-acyl amino acid compounds, antimicrobials, and antifungals. Some particularly suitable examples of additional ingredient include one or more skin care actives selected from the group consisting of vitamin B3 compounds (e.g., niacinamide), n-acyl amino acids (e.g., undecylenoyl phenylalanine), vitamin E compounds (e.g., tocopheryl acetate), palmitoylated dipeptides (e.g., palmitoyl-lysine-threonine), palmitoylated pentapeptides (e.g., palmitoyl-lysine-threonine-threonine-lysine-serine), vitamin A compounds (e.g., retinol and retinyl propionate), and combinations thereof. Other non-limiting examples of optional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/0092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

Conditioning Agents

The compositions herein may include 0.1% to 50% by weight of a conditioning agent (e.g., 0.5% to 30%, 1% to 20%, or even 2% to 15%). Adding a conditioning agent can help provide the composition with desirable feel properties (e.g., a silky, lubricious feel upon application). Some non-limiting examples of conditioning agents include, hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, beeswax derivatives, sterols and phospholipids, salts, isomers and derivatives thereof, and combinations thereof. Particularly suitable examples of conditioning agents include volatile or non-volatile silicone fluids such as dimethicone copolyol, dimethylpolysiloxane, diethylpolysiloxane, mixed C1-30 alkyl polysiloxanes, phenyl dimethicone, dimethiconol, dimethicone, dimethiconol, silicone crosspolymers, and combinations thereof. Dimethicone may be especially suitable, since some consumers associate the feel properties provided by certain dimethicone fluids with good moisturization. Other examples of silicone fluids that may be suitable for use as conditioning agents are described in U.S. Pat. No. 5,011,681.

The compositions herein include 0.05% to 5% of an hydrophobically modified aqueous rheology modifier (e.g., thickening agent) to provide the composition with suitable rheological, stability, and skin feel properties. Some non-limiting examples of thickening agents that may be suitable for use herein include crosslinked polyacrylate polymers, such as PEMULEN EZ-4U, PEMULEN TR-1, PEMULEN TR-2, and certain ULTREZ brand acrylates/C10-30 alkyl acrylate crosspolymers, all available from Lubrizol. Other examples include acrylates vinyl isodecanoate crosspolymer such as STABYLEN 30 sold by 3V, polyacrylate crosspolymer-6 such as SEPIMAX ZEN sold by Seppic®, and sodium polyacryloyldimethyl taurate such as ARISTOFLEX SILK sold by Clariant. In some instances, it may be desirable to exclude polyacrylamide-based thickeners, such as SEPIGEL 305 brand polyacrylamide thickener, as these types of thickeners may destabilize the emulsion.

The rheology modifier of the composition herein may include a medium to long chain fatty-acid derivative emulsifier (e.g., about 12-20 carbon chain, alternatively 16-20 carbon chain). In some examples, the emulsifier can be a non-ionic, stearic acid-derived emulsifier, such as steareth-2 steareth-21, PEG-100 stearate, glycereth-25 pyrrolidonecarboxylic acid isostearate, and combinations of these. A "steric acid-derived emulsifier" is an emulsifier in which at least one of the lipophilic domains of the surfactant is comprised of a saturated 18-carbon chain (similar to stearic acid). These emulsifiers typically contain stearate, steareth, or isostearate in their chemical names and are often derived from stearic acid combined with other chemical moieties. Particularly suitable emulsifiers include stearic-acid derived emulsifiers with a hydrophilic-lipophilic balance (HLB) of 14 or more. The emulsifier may be present in the composition at 0.05% to 5% (e.g., 0.1% to 4%, 0.5% to 3% or even 1% to 2%). In some instances, it may be desirable to exclude certain polyether modified silicone emulsifiers, such a PEG-11 methyl ether dimethicone, PEG-12 dimethicone, PEG/PPG 19/19 dimethicone, or other PEGylated dimethicones, which may destabilize an oil-in-water emulsion.

Method of Use

Methods of using the composition herein involve identifying a target portion of skin on a person in need of treatment and applying the present composition to the target portion of skin over the course of a treatment period. The compositions herein should contain an effective amount of a sucrose ester and a fatty alcohol, in combination. The target portion of skin may be on a facial skin surface such as the forehead, perioral, chin, periorbital, nose, and/or check) or another part of the body (e.g., hands, arms, legs, back, chest). The person in need of treatment is one whose skin exhibits signs of oxidative stress, such as fine lines, wrinkles, hyperpigmentation, uneven skin tone, and/or other visible skin features typically associated with aging. In some instances, the target portion of skin may not exhibit a visible sign of skin aging, but a user (e.g., a relatively young user) may still wish to target such an area of skin, if it is one that typically develops such issues as a person ages. In this way, the present method may be used as a preventative measure to delay the onset of visible signs of skin aging.

The composition may be applied to a target portion of skin and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. When used according to the methods herein, the present compositions can improve the appearance of skin affected by oxidative stress by increasing ATP production in skin cells. Changes in cellular ATP production can be determined according to the method described in more detail below.

A treatment period herein is ideally of sufficient time for the combination of sucrose ester and fatty alcohol present in the composition to increase ATP production in skin cells experiencing oxidative stress, thereby improving the appearance of visible signs of skin aging. The ATP production benefit provided by the present method can be demonstrated by a synergistic increase in ATP production relative to the use of the sucrose ester and fatty alcohol individually. In some instances, the present method may provide a synergistic increase of ATP production of at least 5% (e.g., 10%, 15%, 20%, 25%, or more) relative to the expected increase in ATP production. The treatment period may last for at least 1 week (e.g., about 2 weeks, 4 weeks, 8 weeks, or even 12 weeks). In some instances, the treatment period will extend over multiple months (i.e., 3-12 months). In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a wrinkle or line) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied broadly to one or more skin surfaces. In certain embodiments, the compositions herein may be used as part of a multi-step beauty regimen, wherein the present composition may be applied before and/or after one or more other compositions.

METHODS

Oxidative Stress Test

This test method provides a suitable way to determine the ability of a test agent to improve cellular ATP production in cells subjected to oxidative stress.

Keratinocytes (e.g., H-tert-keratinocytes from University of Texas Southwestern) are cultured in T150 flasks in EpiLife Medium (e.g., catalogue #MEPICFPRF500 from Thermo Fisher Scientific) supplemented with human keratinocyte growth supplement (e.g., catalogue #S-001-5 from Thermo Fisher Scientific) and 1% penicillin/streptomycin (e.g., catalogue #15140-122 from Thermo Fisher Scientific). When the keratinocytes reach ~70% confluency, they are plated out into 96 well plates (white, clear bottom with 20,000 cells/well). Incubate the plates for 24 hours before the experimental stress and treatment are applied.

The 96 well plate is divided into three groups of samples (wells) as follows: (i) no stress and no treatment is applied, (ii) stress is applied but no treatment and (iii) stress and treatment are both applied. In combination experiments, stress plus 2 treatments may be applied. For the no stress/no treatment samples (i.e., group (i) above), the culture medium is simply refreshed. For the stressed samples (i.e., group (ii) and (iii) above), culture medium containing 400 μM hydrogen peroxide (HOOH) is used to replace the medium. For the treatment samples (i.e., group (iii) above), immediately after adding the HOOH, pipette the treatment(s) into the wells from a 100× master stock. Return the plates to the CO2 incubator for 90 minutes before measuring ATP.

ATP is measured by removing the media from the samples and replacing it with ATP Glo® reagent (available from Promega, Madison, WI), or equivalent, per manufacturer's instructions. After 10 minutes of exposure at room temperature, the luminescence of each sample can be measured using a Perkin Elmer ENVISION brand plate reader or equivalent. Luminescent counts are directly proportional to ATP level in the cells. Record the luminescent counts for each sample.

Replicates of each treatment group are averaged together, and standard p-value calculations are used (2-sided, equal variance) to calculate significance. In cases where 2 treatments appear to synergistically enhance ATP levels, the results of the combined treatments can be compared to the sum of the individual treatments to determine a synergy factor. The synergy factor is calculated as the ratio of the observed effect from the combined treatments divided by the sum of the results from each individual treatment. A synergy factor of 1.00 indicates that the combination treatment performed as expected whereas synergy factors >1.00 indicate a synergistic benefit beyond simple additivity/expectation.

The test agents used in the Oxidative Stress Test are limited to relatively low concentrations due to cell toxicity. That is, applying high concentrations of the test agent directly to "unprotected" keratinocytes may kill some of all of the cells, which would obviously skew the test results. Normal human skin has a stratum corneum layer that acts as a barrier to foreign substances and contaminants, thereby protecting the underlying viable epidermis. The stratum corneum has a "brick and mortar" arrangement, in which mature corneocytes (the "bricks") are disposed in a lipid matrix of fatty acids, ceramides, and cholesterol (the "mortar"). In order for a topically applied skin care active to be effective, it must penetrate the stratum corneum to reach the living cells in the viable epidermis. However, penetrating the stratum corneum effectively dilutes the skin care active by anywhere from 10- to 10,000-fold, and only a relatively small amount of the applied active actually reaches the viable epidermis. Since the keratinocytes used in the Oxidative Stress Test do not have a stratum corneum layer to dilute the test agent/skin care active, the test agent must be diluted prior to application to the living cells. Thus, the results observed in the Oxidative Stress Test for a particular concentration of test agent are scalable (e.g., by a factor of 10× to 10,000×), based on the known dilution effects of the human stratum corneum. For example, it is believed that a test agent that exhibits a synergistic effect in the Oxidative Stress Test at a concentration of 10 ppm (0.001%), would provide substantially the same synergistic effect when included in a skin care composition at 0.01%, 0.1%, and/or 1%.

EXAMPLES AND COMBINATIONS

Example 1: Formulations

Table 1 below provides examples of skin care compositions containing a synergistic combination of a sucrose ester and a vitamin $B_3$ compound. The exemplary compositions can be made using conventional methods. In some instances, when the composition is in the form of an oil-in-water emulsion, it may be desirable to make it as follows. Prepare a sucrose ester premix by combining the sucrose ester, pentylene glycol, and QS water and mixing until the sucrose ester is fully dissolved. Heat may be used as appropriate to aid in dissolving the sucrose ester. Separately, the aqueous phase may be prepared by dispersing the thickener(s) and polymeric emulsifier(s) in water. After the thickener(s) is dispersed and homogenous, add any additional emulsifier(s) (e.g., high-HLB emulsifier) to the aqueous phase. Add the remaining aqueous phase ingredients and adjust the pH as desired (e.g., pH 5-7). In a separate container, combine the oil phase ingredients and mix until homogenous, with heating as necessary (e.g., to melt any solid materials). Next emulsify the oil phase into the water phase by slowly adding the oil phase while mixing, continue mixing until the emulsion is fully homogeneous. After the emulsion is fully homogeneous, add any remaining ingredients or powder phase materials while mixing until homogeneous. The sucrose ester pre-mix phase can be added to the batch before or after the emulsification step and then mixing until the batch is homogeneous.

TABLE 1

| INGREDIENTS | A | B | C | D | E | F | G | H |
|---|---|---|---|---|---|---|---|---|
| Hexyldecanol | 5.00 | 5.00 | 5.00 | 5.00 | 5.00 | 5.00 | 5.00 | 5.00 |
| Phytosteryl/octyldodecyl lauroyl glutamate[1] | 1.00 | 1.00 | 1.00 | 1.00 | 1.00 | 1.00 | 1.00 | 1.00 |
| Tocopheryl acetate | 0.50 | 0.50 | 0.50 | 0.50 | 0.50 | 0.50 | 0.50 | 0.50 |
| Dimethicone/vinyl dimethicone crosspolymer[2] | 1.00 | 1.00 | 1.00 | 1.00 | 1.00 | 1.00 | 1.00 | 1.00 |
| Cetearyl glucoside (and) Cetearyl alcohol[3] | — | — | — | — | — | — | — | — |
| Behenyl alcohol | — | — | — | — | — | — | — | — |
| Cetyl alcohol | — | — | — | — | — | — | — | — |
| Stearyl alcohol | — | — | — | — | — | — | — | — |
| Isopropyl isostearate | — | — | — | — | — | — | — | — |
| Isohexadecane | — | — | — | — | — | — | — | — |
| Dimethicone (and) dimethiconol[4] | — | — | — | — | — | — | — | — |
| PEG-11 methyl ether dimethicone[5] | 0.25 | 0.25 | 0.25 | — | 0.25 | 0.25 | 0.25 | 0.25 |
| Polysorbate 20 | — | — | — | — | — | — | — | — |
| Glycereth-25 PCA isostearate | 1.00 | — | 1.00 | 1.00 | 1.00 | 1.00 | 1.00 | 1.00 |
| Stereath-2 | 0.05 | 0.10 | — | 0.05 | 0.05 | 0.05 | 0.05 | 0.05 |
| Stereath-21 | 0.45 | 0.90 | — | 0.45 | 0.45 | 0.45 | 0.45 | 0.45 |
| PEG-100 stearate | — | — | 1.00 | — | — | — | — | — |
| Pentylene glycol | 3.00 | 3.00 | 3.00 | 3.00 | 3.00 | 3.00 | 3.00 | 3.00 |
| Sucrose ester[6] | 1.00 | 1.00 | 1.00 | 1.00 | 1.00 | 1.00 | 1.00 | 1.00 |
| Acrylates/c10-30 alkyl acrylate crosspolymer[7] | 0.10 | 0.10 | 0.10 | 0.10 | 0.10 | 0.10 | 0.10 | — |
| Acrylates/c10-30 alkyl acrylate crosspolymer[8] | 0.40 | 0.40 | 0.40 | 0.40 | 0.20 | — | — | — |
| Acrylates/c10-30 alkyl acrylate crosspolymer[9] | — | — | — | — | — | 0.40 | 0.20 | — |
| Acrylates vinyl isodeconate crosspolymer[10] | — | — | — | — | — | — | — | 0.40 |
| Xanthan gum | — | — | — | — | — | — | — | — |
| Polyacrylamide (and) C13-14 isoparaffin (and) laureth-7[11] | — | — | — | — | — | — | — | — |
| Xylitol | 1.50 | 1.50 | 1.50 | 1.50 | 1.50 | 1.50 | 1.50 | 1.50 |
| Niacinamide | 5.00 | 5.00 | 5.00 | 5.00 | 5.00 | 5.00 | 5.00 | 5.00 |
| Sodium benzoate | 0.05 | 0.05 | 0.05 | 0.05 | 0.05 | 0.05 | 0.05 | 0.05 |
| Disodium EDTA | 0.10 | 0.10 | 0.10 | 0.10 | 0.10 | 0.10 | 0.10 | 0.10 |
| Phenoxyethanol | 0.25 | 0.25 | 0.25 | 0.25 | 0.25 | 0.25 | 0.25 | 0.25 |
| Benzyl alcohol | 0.20 | 0.20 | 0.20 | 0.20 | 0.20 | 0.20 | 0.20 | 0.20 |
| D-panthenol | 1.00 | 1.00 | 1.00 | 1.00 | 1.00 | 1.00 | 1.00 | 1.00 |
| Aminomethyl propanol[+] | 0.40 | 0.40 | 0.40 | 0.40 | 0.40 | 0.40 | 0.40 | 0.40 |
| Undecylenoyl phenylalanine[12] | 0.20 | 0.20 | 0.20 | 0.20 | 0.20 | 0.20 | 0.20 | 0.20 |
| Glycerin | 2.50 | 2.50 | 2.50 | 2.50 | 2.50 | 2.50 | 2.50 | 2.50 |
| Butylene glycol | 2.00 | 2.00 | 2.00 | 2.00 | 2.00 | 2.00 | 2.00 | 2.00 |
| Water | QS | QS | QS | QS | QS | QS | QS | QS |

| | I | J | K | L | M | N | O | P |
|---|---|---|---|---|---|---|---|---|
| INGREDIENTS | | | | Wt % | | | | |
| Hexyldecanol | 5.00 | 5.00 | 1.25 | 1.25 | 0.25 | 5.00 | 1.25 | 0.25 |
| Phytosteryl/octyldodecyl lauroyl glutamate[1] | 1.00 | 1.00 | 1.00 | 1.00 | 1.00 | — | — | — |
| Tocopheryl acetate | 0.50 | 0.50 | 0.50 | 0.50 | 0.50 | 0.50 | 0.50 | 0.50 |
| Dimethicone/vinyl dimethicone crosspolymer[2] | 1.00 | 1.00 | 1.00 | 1.00 | 1.00 | — | — | — |
| Cetearyl glucoside (and) Cetearyl alcohol[3] | — | — | — | — | — | 0.20 | 0.20 | 0.20 |
| Behenyl alcohol | — | — | — | — | — | 0.40 | 0.40 | 0.40 |
| Cetyl alcohol | — | — | — | — | — | 0.32 | 0.32 | 0.32 |

TABLE 1-continued

| | | | | | | | | |
|---|---|---|---|---|---|---|---|---|
| Stearyl alcohol | — | — | — | — | — | 0.48 | 0.48 | 0.48 |
| Isopropyl isostearate | — | — | — | — | — | — | 1.33 | 1.33 |
| Isohexadecane | — | — | — | — | — | — | 3.00 | 3.00 |
| Dimethicone (and) dimethiconol[4] | — | — | — | — | — | 2.00 | 2.00 | 2.00 |
| PEG-11 methyl ether dimethicone[5] | 0.25 | 0.25 | 0.25 | 0.25 | 0.25 | — | 0.25 | 0.25 |
| Polysorbate 20 | 0.5 | 0.5 | — | — | — | — | — | — |
| Glycereth-25 PCA isostearate | 1 | 0.25 | 1 | — | 1 | 1 | 1 | 1 |
| Stereath-2 | 0.1 | 0.025 | 0.05 | 0.1 | — | 0.05 | 0.05 | 0.05 |
| Stereath-21 | 0.09 | 0.225 | 0.45 | 0.9 | — | 0.45 | 0.45 | 0.45 |
| PEG-100 stearate | — | — | — | — | 1 | — | — | — |
| Pentylene glycol | 2 | 2 | 2 | 2 | 2 | 2 | 2 | 2 |
| Sucrose ester[6] | 1 | 1 | 1 | 1 | 1 | 1 | 1 | 1 |
| Acrylates/c10-30 alkyl acrylate crosspolymer[7] | 0.32 | 0.32 | 0.32 | 0.28 | 0.32 | — | — | — |
| Acrylates/c10-30 alkyl acrylate crosspolymer[8] | — | — | — | — | — | — | — | — |
| Acrylates/c10-30 alkyl acrylate crosspolymer[9] | — | — | — | — | — | — | — | — |
| Acrylates vinyl isodeconate crosspolymer[10] | — | — | — | — | — | — | — | — |
| Xanthan gum | 0.05 | 0.05 | 0.05 | 0.05 | 0.05 | — | — | — |
| Polyacrylamide (and) C13-14 isoparaffin (and) laureth-7[11] | 0.60 | 0.60 | 0.60 | 0.60 | 0.60 | 2.00 | 2.00 | 2.00 |
| Xylitol | 1.50 | 1.50 | 1.50 | 1.50 | 1.50 | — | — | — |
| Niacinamide | 5.00 | 5.00 | 5.00 | 5.00 | 5.00 | 5.00 | 5.00 | 5.00 |
| Sodium benzoate | 0.05 | 0.05 | 0.05 | 0.05 | 0.05 | 0.05 | 0.05 | 0.05 |
| Disodium EDTA | 0.10 | 0.10 | 0.10 | 0.10 | 0.10 | 0.10 | 0.10 | 0.10 |
| Phenoxyethanol | 0.25 | 0.25 | 0.25 | 0.25 | 0.25 | 0.25 | 0.25 | 0.25 |
| Benzyl alcohol | 0.20 | 0.20 | 0.20 | 0.20 | 0.20 | 0.20 | 0.20 | 0.20 |
| D-panthenol | 1.00 | 1.00 | 1.00 | 1.00 | 1.00 | 1.00 | 1.00 | 1.00 |
| Aminomethyl propanol[+] | 0.30 | 0.30 | 0.30 | 0.30 | 0.30 | — | — | — |
| Undecylenoyl phenylalanine[12] | 0.20 | 0.20 | 0.20 | 0.20 | 0.20 | — | — | — |
| Glycerin | 2.50 | 2.50 | 2.50 | 2.50 | 2.50 | 7.00 | 7.00 | 7.00 |
| Butylene glycol | 2.00 | 2.00 | 2.00 | 2.00 | 2.00 | — | — | — |
| Water | QS | QS | QS | QS | QS | QS | QS | QS |

| INGREDIENTS | Q | R | S | T | U | V | W | X |
|---|---|---|---|---|---|---|---|---|
| Hexyldecanol | 5.00 | 10.00 | 2.50 | 0.0001 | 0.0040 | — | — | 4.50 |
| Zinc Ricinoleate | — | — | — | — | — | 0.25 | — | 0.25 |
| Potassium 12-Hydroxystearate | — | — | — | — | — | — | 0.25 | 0.25 |
| Phytosteryl/octyldodecyl lauroyl glutamate[1] | 1.00 | 1.00 | 1.00 | 1.00 | 1.00 | 1.00 | 1.00 | 1.00 |
| Tocopheryl acetate | 0.50 | 0.50 | 0.50 | 0.50 | 0.50 | 0.50 | 0.50 | 0.50 |
| Dimethicone/vinyl dimethicone crosspolymer[2] | 1.00 | 1.00 | 1.00 | 1.00 | 1.00 | 1.00 | 1.00 | 1.00 |
| Cetearyl glucoside (and) Cetearyl alcohol[3] | — | — | — | — | — | — | — | — |
| Behenyl alcohol | — | — | — | — | — | — | — | — |
| Cetyl alcohol | — | — | — | — | — | — | — | — |
| Stearyl alcohol | — | — | — | — | — | — | — | — |
| Isopropyl isostearate | — | — | — | — | — | — | — | — |
| Isohexadecane | — | — | — | — | — | — | — | — |
| Dimethicone (and) dimethiconol[4] | — | — | — | — | — | — | — | — |
| PEG-11 methyl ether dimethicone[5] | 0.25 | 0.25 | 1.25 | 0.25 | 0.25 | 0.25 | 0.25 | 0.25 |
| Polysorbate 20 | 0.50 | — | — | 0.50 | 0.50 | 0.50 | 0.50 | 0.50 |
| Glycereth-25 PCA isostearate | — | 1.00 | 1.00 | — | — | — | — | — |
| Stereath-2 | — | 0.05 | 0.05 | — | — | — | — | — |
| Stereath-21 | — | 0.45 | 0.45 | — | — | — | — | — |
| PEG-100 stearate | — | — | — | — | — | — | — | — |
| Pentylene glycol | 3.00 | 3.00 | 4.00 | 3.00 | 3.00 | 3.00 | 3.00 | 3.00 |
| Sucrose ester[6] | 0.125 | 0.25 | 10.0 | 0.0004 | 0.0001 | 0.25 | 0.25 | 0.125 |
| Acrylates/c10-30 alkyl acrylate crosspolymer[7] | 0.28 | 0.10 | 0.10 | 0.28 | 0.28 | 0.28 | 0.28 | 0.28 |
| Acrylates/c10-30 alkyl acrylate crosspolymer[8] | — | 0.40 | 0.40 | — | — | — | — | — |
| Acrylates/c10-30 alkyl acrylate crosspolymer[9] | — | — | — | — | — | — | — | — |
| Acrylates vinyl isodeconate crosspolymer[10] | — | — | — | — | — | — | — | — |
| Xanthan gum | 0.05 | — | — | 0.05 | 0.05 | 0.05 | 0.05 | 0.05 |
| Polyacrylamide (and) C13-14 isoparaffin (and) laureth-7[11] | 0.60 | — | — | 0.60 | 0.60 | 0.60 | 0.60 | 0.60 |
| Xylitol | 1.50 | 1.50 | 1.50 | 1.50 | 1.50 | 1.50 | 1.50 | 1.50 |
| Niacinamide | 5.00 | 5.00 | 5.00 | 5.00 | 5.00 | 5.00 | 5.00 | 5.00 |
| Sodium benzoate | 0.05 | 0.05 | 0.05 | 0.05 | 0.05 | 0.05 | 0.05 | 0.05 |
| Disodium EDTA | 0.10 | 0.10 | 0.10 | 0.10 | 0.10 | 0.10 | 0.10 | 0.10 |
| Phenoxyethanol | 0.25 | 0.25 | 0.25 | 0.25 | 0.25 | 0.25 | 0.25 | 0.25 |
| Benzyl alcohol | 0.20 | 0.20 | 0.20 | 0.20 | 0.20 | 0.20 | 0.20 | 0.20 |
| D-panthenol | 1.00 | 1.00 | 1.00 | 1.00 | 1.00 | 1.00 | 1.00 | 1.00 |
| Aminomethyl propanol[+] | 0.30 | 0.40 | 0.40 | 0.20 | 0.20 | 0.20 | 0.20 | 0.20 |

TABLE 1-continued

| | | | | | | | | |
|---|---|---|---|---|---|---|---|---|
| Undecylenoyl phenylalanine[12] | 0.20 | 0.20 | 0.20 | 0.20 | 0.20 | 0.20 | 0.20 | 0.20 |
| Glycerin | 2.50 | 2.50 | 2.50 | 2.50 | 2.50 | 2.50 | 2.50 | 2.50 |
| Butylene glycol | 2.00 | 2.00 | 2.00 | 2.00 | 2.00 | 2.00 | 2.00 | 2.00 |
| Water | QS | QS | QS | QS | QS | QS | QS | QS |

| INGREDIENTS | Y | Z |
|---|---|---|
| Hexyldecanol | 5.00 | 5.00 |
| Zinc Ricinoleate | — | — |
| Potassium 12-Hydroxystearate | — | — |
| Phytosteryl/octyldodecyl lauroyl glutamate[1] | 1.00 | 1.00 |
| Tocopheryl acetate | 0.50 | 0.50 |
| Dimethicone/vinyl dimethicone crosspolymer[2] | — | — |
| Cetearyl glucoside (and) Cetearyl alcohol[3] | — | — |
| Behenyl alcohol | — | — |
| Cetyl alcohol | — | — |
| Stearyl alcohol | — | — |
| Isopropyl isostearate | — | — |
| Isohexadecane | — | — |
| Dimethicone (and) dimethiconol[4] | — | — |
| PEG-11 methyl ether dimethicone[5] | 0.25 | 0.25 |
| Polysorbate 20 | — | — |
| Glycereth-25 PCA isostearate | — | — |
| Stereath-2 | 0.1 | 0.1 |
| Stereath-21 | 0.9 | 0.9 |
| PEG-100 stearate | — | — |
| Pentylene glycol | 3.00 | 3.00 |
| Sucrose ester[6] | 1.0 | 1.0 |
| Acrylates/c10-30 alkyl acrylate crosspolymer[7] | 0.24 | 0.24 |
| Acrylates/c10-30 alkyl acrylate crosspolymer[8] | — | — |
| Acrylates/c10-30 alkyl acrylate crosspolymer[9] | — | — |
| Acrylates vinyl isodeconate crosspolymer[10] | — | — |
| Polyacrylate crosspolymer-6[13] | 0.4 | — |
| Sodium polyacryloyldimethyl taurate[14] | — | 0.4 |
| Xanthan gum | — | — |
| Polyacrylamide (and) C13-14 isoparaffin (and) laureth-7[11] | — | — |
| Xylitol | — | — |
| Niacinamide | 5.00 | 5.00 |
| Sodium benzoate | 0.05 | 0.05 |
| Disodium EDTA | 0.10 | 0.10 |
| Phenoxyethanol | 0.25 | 0.25 |
| Benzyl alcohol | 0.20 | 0.20 |
| D-panthenol | 1.00 | 1.00 |
| Aminomethyl propanol[+] | 0.30 | 0.40 |
| Undecylenoyl phenylalanine[12] | 0.20 | 0.20 |
| Glycerin | 2.50 | 2.50 |
| Butylene glycol | 2.00 | 2.00 |
| Water | QS | QS |

[+]Balance to approximate neutral pH 5-7
[1]ELDEW PS-203 available from Ajinomoto
[2]KSG-16 available from Shin-Etsu
[3]EMULGADE PL68/50 available from BASF
[4]XIAMETER PMX-1503 available from Dow Corning
[5]KF-6011 available from Shin-Etsu
[6]BC10034 from BASF
[7]CARBOPOL ULTREZ 20 available from Lubrizol
[8]PEMULEN TR-1 available from Lubrizol
[9]PEMULEN EZ-4U available from Lubrizol
[10]STABLYEN 30 available from 3V
[11]SEPIGEL 305 available from Seppic
[12]SEPIWHITE available from Seppic
[13]SEPIMAX ZEN available from Seppic
[14]ARISTOFLEX SILK available from Clariant

Example 2—Criticality of Ratio of Sucrose Ester to Fatty Alcohol

This example demonstrates the importance of providing including the sucrose ester and fatty alcohol at a suitable ratio in the skin care composition. The fatty alcohol tested in this example is hexyldecanol and the sucrose ester is a mixture of sucrose laurate and sucrose dilaurate (BC10034 from BASF). Ratios of fatty alcohol to sucrose ester of 1:1, 5:1, 50:1, and 1:5 were tested according to the Oxidative Stress Test described above. A summary of the results of the test are provided in Tables 2, 3, 4, and 5 below. Test legs that have a synergy value of greater than 1 and a p-value of less than 0.05 are considered synergistic. Synergy values of at least 1.05 are preferred (e.g., at least 1.1, 1.2, 1.3, 1.4, 1.5, or even 1.6 or more).

TABLE 2

| 1:1 ratio | | | |
|---|---|---|---|
| | Fatty Alcohol (1 ppm) | Sucrose Ester (1 ppm) | FA + SE (1:1) |
| Measured ATP level | 534.3 | 44.7 | 1034.0 |
| Expected ATP level | n/a | n/a | 579.0 |
| Synergy Factor | n/a | n/a | 1.79 |
| p-value | n/a | n/a | 0.004 |

TABLE 3

| 5:1 ratio | | | |
|---|---|---|---|
| | Fatty Alcohol (5 ppm) | Sucrose Ester (1 ppm) | FA + SE (5:1) |
| Measured ATP level | 708.0 | 44.7 | 1191.7 |
| Expected ATP level | n/a | n/a | 752.7 |
| Synergy Factor | n/a | n/a | 1.58 |
| p-value | n/a | n/a | 0.008 |

TABLE 4

| 50:1 ratio | | | |
|---|---|---|---|
| | Fatty Alcohol (50 ppm) | Sucrose Ester (1 ppm) | FA + SE (50:1) |
| Measured ATP level | 962.3 | 44.7 | 965.3 |
| Expected ATP level | n/a | n/a | 1007.0 |
| Synergy Factor | n/a | n/a | 0.96 |
| p-value | n/a | n/a | 0.518 |

TABLE 5

| 1:5 ratio | | | |
|---|---|---|---|
| | Fatty Alcohol (0.2 ppm) | Sucrose Ester (1 ppm) | FA + SE (1:5) |
| Measured ATP level | 368.3 | 44.7 | 434.3 |
| Expected ATP level | n/a | n/a | 413.0 |
| Synergy Factor | n/a | n/a | 1.05 |
| Synergy p-value | n/a | n/a | 0.708 |

As can be seen in Table 2, 3, 4, and 5, only ratios of fatty alcohol to sucrose ester of 1:1 and 5:1 provided a statistically significant synergistic improvement in ATP production. These data suggest that only certain ratios of fatty alcohol to sucrose ester (e.g., between 50:1 and 1:5) can provide the desired synergistic increase in ATP production in oxidatively stressed cells. Thus, the skin appearance benefits provided by a skin care composition intended to treat the signs of skin aging associated with oxidative stress may be greatly enhanced when the composition includes a suitable combination of fatty alcohol and sucrose ester.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin care composition, comprising:

a) a sucrose ester chosen from sucrose laurate, sucrose dilaurate, sucrose trilaurate, or mixtures thereof;

b) hexyldecanol; and c) a dermatologically acceptable carrier, wherein the fatty alcohol and sucrose ester are present at a weight ratio of 1:1 to 5:1, based on the weight of the composition, and the combination of sucrose ester and fatty alcohol has a synergy factor of at least 1.1 according to the Oxidative Stress Test.

2. The skin care composition of claim 1, wherein the sucrose ester comprises a mixture of sucrose laurate and sucrose dilaurate.

3. The skin care composition of claim 2, wherein sucrose laurate is present at about 55% to about 80%, by weight of the sucrose ester and the sucrose dilaurate is present at about 20% to about 45% by weight of the sucrose ester.

4. The skin care composition of claim 1, wherein the composition further comprises at least one additional ingredient chosen from vitamins, minerals, peptides, sugar amines, sunscreen agents, oil control agents, flavonoid compounds, anti-oxidants, preservatives, protease inhibitors, tyrosinase inhibitors, anti-inflammatory agents, moisturizing agents, exfoliating agents, skin lightening agents, lubricants, anti-acne actives, chelating agents, anti-wrinkle actives, anti-atrophy actives, phytosterols, N-acyl amino acid compounds, antimicrobials, and antifungals, conditioning agents, emulsifiers, rheology modifiers, or mixtures thereof.

5. The skin care composition of claim 4, wherein the additional ingredient is a skin care active chosen from vitamin B3 compounds, undecylenoyl phenylalanine, vitamin E compounds, palmitoylated dipeptides, palmitoylated pentapeptides, vitamin A compounds, or mixtures thereof.

6. The skin care composition of claim 4, wherein the composition further comprises a rheology modifier chosen from the group consisting of acrylates/C10-30 alkyl acrylate crosspolymer, acrylates vinyl isodeconate crosspolymers, polyacrylate crosspolymer-6, sodium polyacryloyldimethyl taurate, or mixtures thereof.

7. The skin care composition of claim 4, wherein the composition further comprises an emulsifier chosen from glycereth-25 pyrrolidonecarboxylic acid isostearate, PEG-100 stearate, steareth-2, steareth-21, or mixtures thereof.

8. A method of improving cellular energy levels in skin cells affected by oxidative stress, comprising:

a) identifying a target portion of skin where treatment is desired; and b) applying the skin care composition of claim 1.

9. The method of claim 8, wherein the sucrose ester and the fatty alcohol are each present at about 0.0001% to about 10%, by weight of the composition.

10. The method of claim 8, wherein the fatty alcohol is present at about 0.0001% to about 10%, by weight of the composition.

11. The method of claim 8, wherein the target portion of skin exhibits a sign of oxidative stress and the composition is applied over the course of a treatment period.

12. The method of claim 11, wherein the treatment period is at least 4 weeks and the composition is applied at least once per day.

* * * * *